United States Patent [19]

Barrow et al.

[11] 3,977,943

[45] Aug. 31, 1976

[54] ANTIBIOTICS

[75] Inventors: Kevin David Barrow; Graham Mellows, both of London, England

[73] Assignee: Beecham Group Limited, Great Britain

[22] Filed: July 7, 1975

[21] Appl. No.: 593,322

Related U.S. Application Data

[60] Continuation of Ser. No. 455,291, March 27, 1974, abandoned, which is a division of Ser. No. 261,042, June 8, 1972, abandoned.

[30] Foreign Application Priority Data

June 12, 1971 United Kingdom............... 27653/71

[52] U.S. Cl. .................................................. 195/96
[51] Int. Cl.² ........................................ A21K 21/00
[58] Field of Search .................. 195/80 R, 80 T, 96; 260/559 AT; 424/123, 124

[56] References Cited

UNITED STATES PATENTS

| 2,847,471 | 8/1958 | Vandeputte et al. ......... 260/559 AT |
| 3,011,947 | 12/1961 | Preud'Homme et al. ........... 424/123 |

*Primary Examiner*—A. Louis Monacell
*Assistant Examiner*—R. B. Penland

[57] ABSTRACT

Antibacterial substances, pseudomonic acid, an isomer thereof, and pseudomonic acid I, are isolated by growing *Pseudomonas fluorescens* under aerobic conditions, precipitating and removing unwanted barium salts, extracting the culture medium to isolate a mixture of the three acids and separating each acid therefrom.

14 Claims, 3 Drawing Figures

ANTIBIOTICS

CROSS-REFERENCE

This is a continuation of Ser. No. 455,291 filed Mar. 27, 1974, now abandoned, which is a divisional application of Ser. No. 261,042, filed June 8, 1972, which application is abandoned.

This invention relates to antibiotics produced by the bacterium *Pseudomonas fluorescens*

It has been known for many years that the bacterium *Pseudomonas fluorescens* produces inhibitory substances, and a convenient review of the published work on the subject can be found in the book "Antibiotics" by H. W. Florey, E. B. Chain, N. G. Heatley, M. A. Jennings, A. G. Saunders, E. P. Abraham, and M. E. Florey, published by the Oxford University Press (1949) Volume 1. We have now succeeded in isolating a mixture of inhibitory substances and in separating the mixture into three components, two of which are isomeric.

The present invention therefore provides a mixture of three compounds, each in substantially pure form, two of which compounds pseudomonic acid and its isomer, having the formula (I):

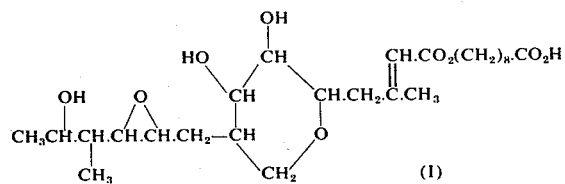

and the third compound, pseudomonic acid I having the formula (II)

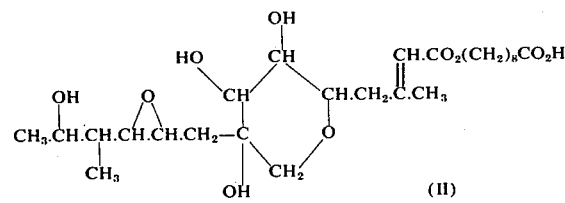

The methyl ester of one isomer of formula (I) may readily be crystallised. We have named this isomer of formula (I) "pseudomonic acid" and the compound of formula (II) "pseudomonic acid I", and they will be referred to as such hereinafter.

These compounds may each be isolated individually. Thus the present invention also provides, in substantially pure form, pseudomonic acid of formula (I) above, and salts and esters thereof.

Figure 1A:
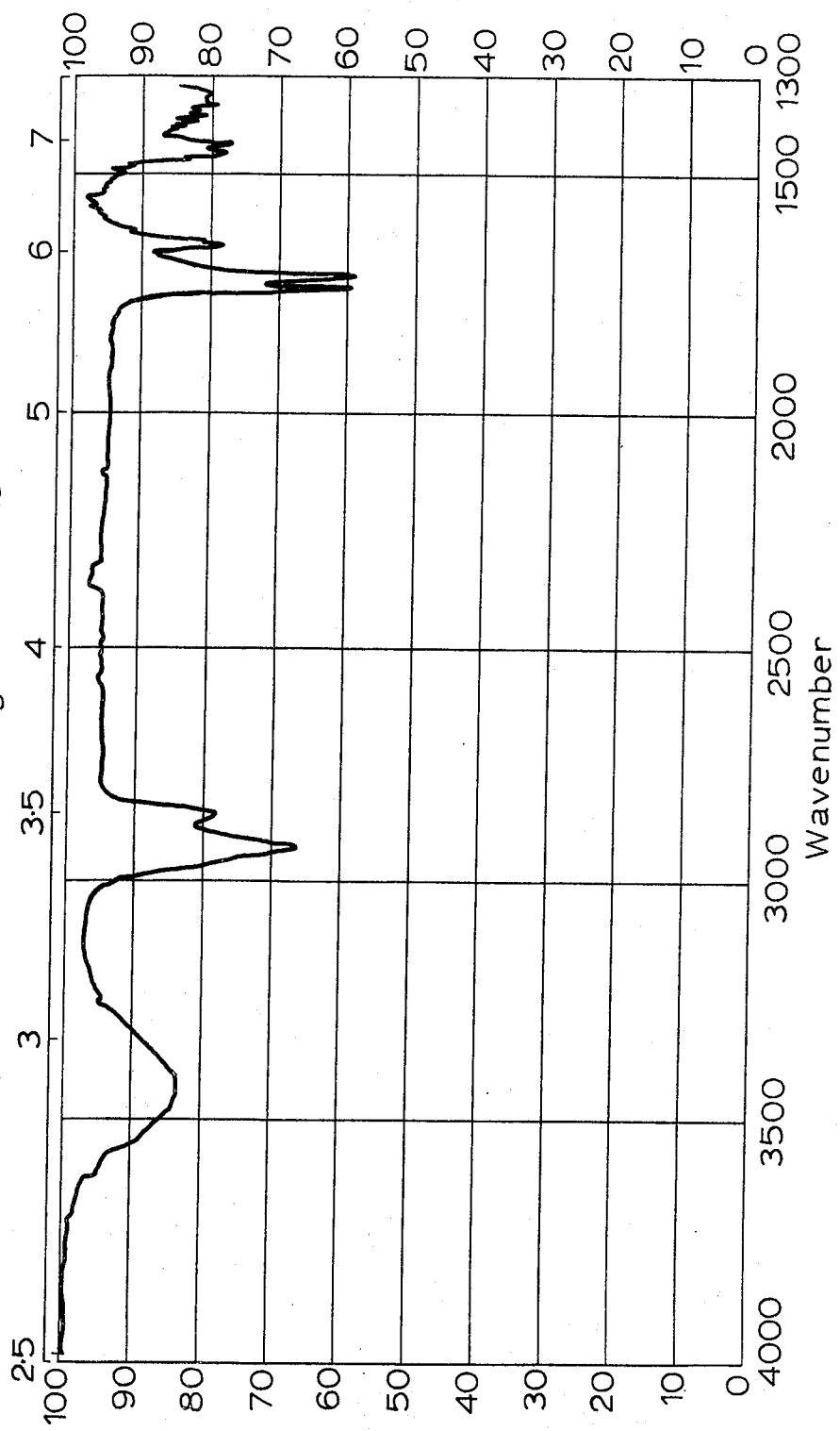
Figure 1B:
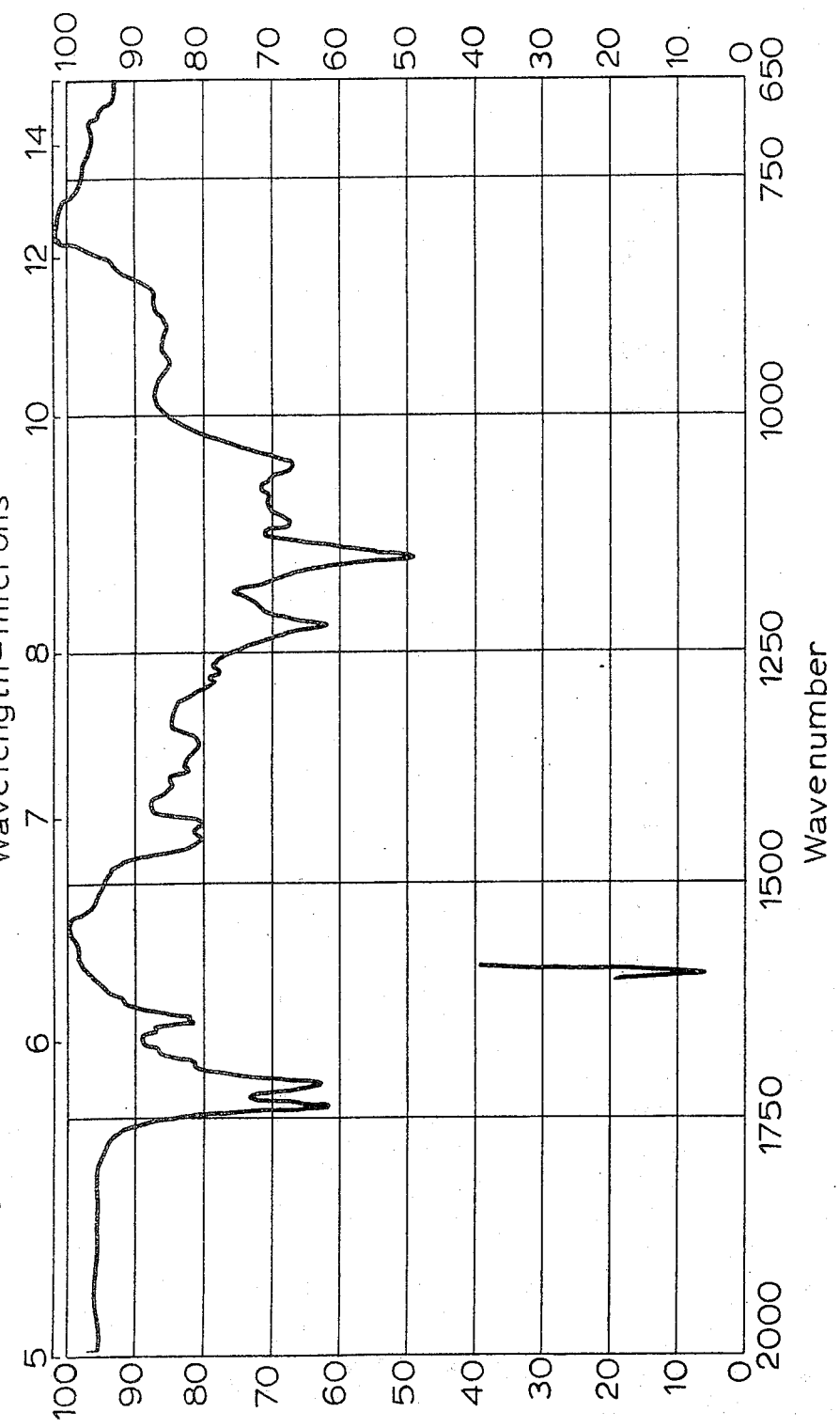
Figure 2:
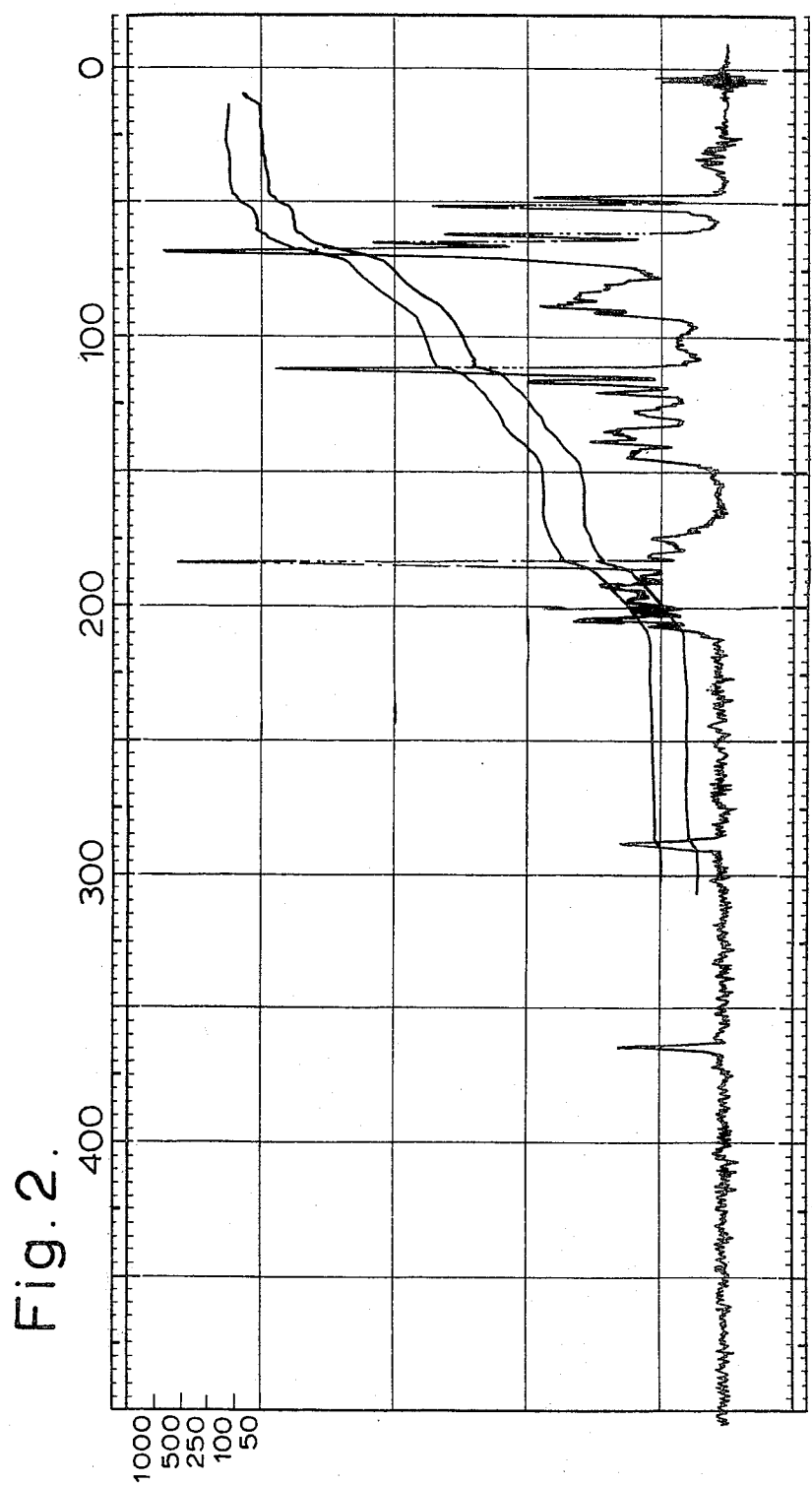

Pseudomonic acid is conveniently characterised as its crystalline methyl ester, which methyl ester has an infra-red spectrum as shown in FIGS. 1A and 1B of the accompanying drawings and a proton magnetic resonance spectrum as shown in FIG. 2 of the accompanying drawings.

Pseudomonic acid has antibacterial activity and the activity appears to be associated with the presence of the free carboxyl group. Thus the salts of pseudomonic acid are active whereas the methyl and p-bromophenacyl esters are less active. Hence the present invention also provides salts of pseudomonic acid and other derivatives of the free carboxyl group which are readily hydrolysed to give the parent pseudomonic acid.

It is believed that the compound represented by formula (I) above can exist in two isomeric forms, having cis- and trans-configuration of the double bond, and that pseudomonic acid as characterised by its crystalline methyl ester in the FIGS. 1 and 2 is the trans-isomer.

The present invention also provides in substantially pure form, pseudomonic acid I of formula (II) above and salts and esters thereof.

Also included within the scope of the present invention is a process for the preparation of the compounds of formulae (I) and (II) in substantially pure form, which process comprises growing *Pseudomonas fluorescens* under aerobic conditions on or in a culture medium containing inorganic salts and sources of assimilable carbon and nitrogen until the culture medium exhibits at least detectable antibacterial activity thereafter adding a source of barium ions to the culture medium and removing the resultant precipitated material therefrom, extracting the culture medium with an organic solvent for the active materials, dissolved in the culture medium, extracting the resultant organic solution with water at a pH between 7 and 9, evaporating the water to leave a solid residue, separating this residue into active and substantially non-active fractions, combining the resultant active fractions thereby producing a mixture of three different acids.

In the above-defined process, the cultivation step where *Pseudomona fluorescens* is grown is conventional. All strains of this organism known to us produce pseudomonic acid to a greater or lesser extent, but one suitable public strain is *pseudomona fluorescens* N.C.I.B. 10586 (NCIB = National Collection of Industrial Bacteria).

However, we regard the next step, i.e. the addition of a source of barium ions to the culture medium as being the step which enables separation of the active components to be carried out efficiently. It appears that the major proportion of the active culture fluid is converted in this step to soluble barium salts (which in itself is surprising since most barium salts are water-insoluble) while the non-active components are left behind as an insoluble precipitate.

After the removal of the precipitate the activity is extracted from the aqueous solution by extraction with a suitable solvent. Suitable solvents can be found by trial and error, but we find that isobutylmethyl ketone (IBMK) is a good solvent. Other solvents include ether containing 5% ethanol, and also chloroform (although these two are not as efficient as IBMK).

The organic solution is then extracted with water at an alkaline pH and the salts of the active materials are obtained by evaporating the water. If desired, the extraction with organic solvent followed by alkali can be repeated several times to ensure efficient extraction of active materials.

The separation of inactive contaminants from the resulting mixture of salts can be achieved either by ion-exchange chromatography of the crude salt mixture or by esterifying the salt mixture and subjecting the esterified mixture to silica gel chromatography. When using ion-exchange methods we find that a polystyrene resin column eluted with a gradient of 0.01N methanolic ammonia in 0.01N aqueous ammonia is a suitable system. Using this system, a series of low molecular weight inactive acids are eluted first, followed by the active fractions (30–60% elution).

In a further aspect, the present invention provides a process for the preparation of pseudomonic acid, in substantially pure form which process comprises producing the active fraction as in the previous aspect of the invention, esterifying this fraction thereby producing a mixture of esters of three different acids, separating pseudomonic acid ester from the mixture and de-esterifying said ester, thereby producing pseudomonic acid.

Furthermore, the present invention provides a process for the formation of pseudomonic acid I in substantially pure form which process comprises esterifying the said active fraction, thereby producing a mixture of esters of three different acids, separating pseudomonic acid I ester from the mixture and de-esterifying said ester, thereby producing pseudomonic acid I.

In order to carry out the processes of the last two embodiments of this invention, the active fraction is esterified e.g. by conversion to the methyl esters, and the ester mixture resolved into its three components. This may be achieved by thin layer chromatography in the conventional way e.g. on silica gel developed by chloroform/isopropanol (9:1). This separates the ester of pseudomonic acid I, which is present in minor amount, and the pseudomonic acid methyl ester can be crystallised from the remaining mixture.

De-esterification of each component will vary according to the particular ester chosen. With the p-bromophenacyl ester the method of Sheehan et al. J. Org. Chem (1964) Vol. 29 p. 2006 may be employed (i.e. treatment with sodium thiophenoxide).

The invention will now be illustrated in the following Examples:

EXAMPLE 1

Isolation of Antibacterially active fractions

*Pseudomonas fluorescens*, strain NCIB. 10586 was grown in submerged culture at 30°C in a medium containing 1% corn steep liquor and 0.5% glucose in a basic salts solution. The maximum yield of the antibiotic occurred after 24 hours and all of the detectable activity was in the culture fluid. After the addition of barium chloride (0.5%) the cells and precipitated non-active material were removed by centrifugation. The activity was progressively concentrated by partitioning into isobutylmethyl ketone (IBMK) (0.2 vol) at pH 4.5 water (0.8 vol) at pH 8.5, and then IBMK (0.25 vol) at pH 4.5 followed by evaporation to a small volume under reduced pressure. After a further partition into water at pH 8.5 and then adjustment to pH 7–8 the aqueous solution was freeze dried to give a mixture of sodium salts which could be stored at 0°C for several months, without loss of activity.

The antibiotic extract was stable within the range pH 4–9 at 37°C for 24 hours. Outside these limits rapid loss of activity occurred. The mixture of sodium salts showed a wide antibacterial spectrum against Gram positive and Gram negative bacteria, showed low toxicity and was bacteriostatic against *S. aureus* (N.C.T.C.6571) and *E. coli* (M.R.E. 600).

Further purification of the crude acid mixture was effected by chromatography on Amberlite XAD-2 polystyrene resin with a linear gradient produced by adding 0.0lN methanolic ammonia, to 0.0lN aqueous ammonia. A series of low molecular weight acids was eluted first followed by fractions (30–60% elution) that possessed the major part of the antibacterial (biological) activity.

EXAMPLE 2

Purification of Pseudomonic acid and Pseudomonic Acid I.

The biologically active fractions as produced in Example 1 upon methylation with diazomethane in ether showed two spots by thin layer chromatography corresponding to methyl pseudomonate plus its isomer and the minor component methyl pseudomonate-I (ratio ca 9:1 by wt.).

Methyl pseudomonate plus its isomer (ca 9 parts by wt.) was separated from methyl pseudomonate-I (ca. 1 part by wt.) by preparative layer silica gel ($GF_{245}$) chromatography on on development with chloroform/isopropanol (9:1). 50% by wt. of methyl pseudomonate was recovered from the mixture with its isomer, by crystallisation from benzene/petroleum ether to give colourless needles m.p. 76.5°–78°.

Elemental analysis indicated the formula $C_{27}H_{46}O_9$ (Found: C, 62.8; H, 8.9. $C_{27}H_{46}O_9$ required C, 63.0; H, 9.0%), and the ester is optically active ($[\alpha]_D^{24} - 9°$ (C, 1.5 in chloroform). Analysis of the oily p-bromophenacyl ester indicated a formula $C_{34}H_{49}BrO_{10}$ (Found: C, 58.1; H, 6.9 $C_{34}H_{49}BrO_{10}$ requires C, 58.5; H, 7.0%). Hence the formula of the parent monocarboxylic acid, pseudomonic acid, is $C_{26}H_{44}O_9$. Further support for this derived from the mass spectrum of the methyl ester which showed the expected molecular ion at m/e 514. The infra-red spectrum of the methyl ester (FIG. 1) showed $\nu$ max. ($CCl_4$) 3440 (hydroxyl), 1740 (ester), 1715 and 1650 cm$^{-1}$ ($\alpha,\beta$-unsaturated ester). The u.v. spectrum ($\lambda$ max (EtOH)221.5nm ($\epsilon$ 13,400) confirms the presence of the $\alpha,\beta$-unsaturated ester linkage. The NMR spectrum (FIG. 2) showed the presence of two secondary methyl groups ($\gamma$ 9.09, 8.81), an olefinic methyl group ($\gamma$ 6.40) and an olefinic proton ($\gamma$ 4.32).

Acetylation of the methyl ester with pyridine/acetic anhydride affords a triacetate $C_{33}H_{52}O_{12}$, which absorbs 1 mole of hydrogen giving a dihydro derivative $C_{33}H_{54}O_{12}$ on catalytic hydrogenation. Reduction of the methyl ester with $LiAlH_4$ in tetrahydrofuran afforded 1,9-dihydroxynonanoate m.p. 46° (bis-phenylcarbamate derivative m.p. 168°–9°). Treatment of the p-bromophenacyl ester with $KMnO_4/NaIO_4$ gave p-bromophenacyl- 9-hydroxynonanoate, $C_{17}H_{23}BrO_4$, m.p. 77.5°–78° (Found: C, 55.1; H, 6.4. $C_{12}H_{23}BrO_4$ requires C, 55.0; H, 6.2%). Mild base hydrolysis of the methyl ester yielded methyl 9-hydroxynonanoate (oil) $C_{10}H_{20}O_3$. Further confirmation of the presence of the 9-hydroxynonanoate unit in pseudomonic acid is provided by the mass spectrum of the methyl ester. Mass measurement of the fragment at m/e 327 gave 327.18059 ($C_{17}H_{27}O_6$ requires 327.18059 corresponding to the loss of $-O(CH_2)_8CO_2CH_3$ from the molecular ion.

EXAMPLE 3

The following is a summary of further observations which lead us to postulate structures for pseudomonic acid and pseudomonic acid 1.

a. The presence of the $C_9$ unit in pseudomonic acid is confirmed by the reactions described in Example 2.

b.

i. Attachment of $C_9$ Unit to Rest of Molecule.

That the $C_9$ unit is attached to the rest of the molecule through a α,β-unsaturated ester linkage to which is attached a —$CH_3$ group (n.m.r. chemical shift in methyl pseudomonate and certain derivatives) was proved by the following observations:

Treatment of a hydroxyl protected derivative of methyl pseudomonate with (a) osmium tetroxide in pyridine, (b) aqueous sodium metabisulphate and (c) sodium periodate in aqueous ethanol gave a compound of formula:

$$OHC.CO_2CH_2(CH_2)_6CH_2CO_2CH_3$$

[characterised by analysis, nuclear magnetic resonance, and infra-red spectra; semi-carlozone derivative m.p. 164°–165.5°] and also a nucleus methyl ketone derivative. This also proves that the —$CH_3$ group is attached to the β-carbon of the α,β-unsaturated ester system.

ii. Confirmation of Double Bond.

Methyl pseudomonate and its triacetate derivative absorb 1 mole hydrogen giving the respective dihydro derivatives, on catalytic hydrogenation showing only end absorption in the ultra-violet spectrum.

iii. Stereochemistry Around Double Bond

That the double bond was trans aligned was derived from the literature values of chemical shifts (nuclear magnetic resonance) of cis and trans $CH_3$ groups attached to double bonds of this type.

c. Nature of Functionalities in Rest of Molecule a. Proof of Glycol System i. Methyl pseudomonate forms an acetonide derivative, characterised by analysis, nuclear magnetic resonance, infra-red and ultra-violet spectra.

ii. Treatment of methyl pseudomonate with sodium periodate in aqueous ethanol gave a dialdehyde as sole product. Hence a glycol system is present and must be in a ring.

iii. This was also confirmed by n.m.r. double resonance experiments on the triacetate and tribenzoate derivatives, b. Proof of Epoxide i. The presence of the epoxide was inferred from chemical shifts, in the n.m.r. spectra of methyl pseudomate and derivatives, of the two attached protons. This was confirmed by n.m.r. double resonance and indor experiments.

c. Part structure

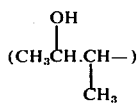

was inferred from the chemical shifts of the relevant protons (n.m.r.) in methyl pseudomonate acetonide derivative and the oxidation product, methyl pseudomonate acetoxide ketone derivative, with part structure

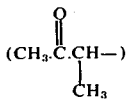

D. Using indor and double resonance techniques in the n.m.r. spectra of the nucleus methyl ketone triacetate and tribenzoate derivatives, the structure of the nucleus methyl ketone was deduced and hence the structure of pseudomonic acid shown to be as formula (I) herein.

PSEUDOMONIC ACID I

The spectra of methyl pseudomonate I and its tri-acetate derivative (mass spectrum, ultra-violet, n.m.r. and infra-red) indicated its close relationship to methyl pseudomonate and that possessed an additional hydroxyl group.

The structure shown in formula (II) herein was deduced from n.m.r. double resonance experiments on the triacetate derivative of the nucleus methyl ketone.

We claim:

1. A process for the preparation of antibacterially active substances which process comprises growing *Pseudomonas fluorescens* under aerobic conditions on or in a culture medium containing inorganic salts and sources of assimilable carbon and nitrogen until the culture medium exhibits at least detectable antibacterial activity, thereafter adding a source of barium ions to the culture and removing the resultant precipitated material therefrom, extracting the culture medium with an organic solvent for the active materials dissolved in the culture medium, extracting the resultant organic solution with an aqueous alkaline solution, and isolating therefrom the antibacterially active fraction.

2. A process according to claim 1 wherein the aqueous alkaline solution is water at a pH between 7 and 9, and which further comprises evaporating the water to leave a solid residue of salts and separating this salt mixture into active and substantially non-active fractions.

3. A process according to claim 2 wherein the active constituents are separated from the mixture of active and inactive salts by ion-exchange chromatography.

4. A process according to claim 3 wherein the ion-exchange system comprises a polystyrene resin with a linear gradient produced by adding from 0.005N to 0.05N methanolic ammonia to from 0.005N to 0.05N aqueous ammonia.

5. A process according to claim 2 wherein the active constituents are separated from the mixture of active and inactive salts by esterifying the salt mixture and subjecting the esterified mixture to silica gel chromatography.

6. A process according to claim 1 wherein the strain of *Pseudomonas fluorescens* which is grown is *Pseudomonas fluorescens* N.C.I.B. 10586.

7. A process according to claim 1 wherein the organic solvent is iso-butylmethyl ketone.

8. A process according to claim 1 wherein the source of barium ions is barium chloride which converts the major proportion of the active culture medium to soluble barium salts.

9. A process for the production of pseudomonic acid in substantially pure form, which process comprises growing *Pseudomonas fluorescens* under aerobic conditions on or in a culture medium containing inorganic salts and sources of assimilable carbon and nitrogen until the culture medium exhibits at least detectable antibacterial activity, thereafter adding a source of barium ions to the culture and removing the resultant precipitated material therefrom, extracting the culture medium with a organic solvent for the active materials dissolved in the culture medium, extracting the resultant organic solution with an aqueous alkaline solution, esterifying the active fraction thereby producing a mixture of esters of three different acids, separating pseudomonic acid ester from the mixture and de-esterifying said ester, thereby producing pseudomonic acid.

10. A process according to claim 9 wherein the active fraction is methylated, thereby producing a mixture of methyl ester.

11. A process according to claim 9 wherein the pseudomonic acid ester is separated from the mixture of esters by:
   a. separating the esters of pseudomonic acid and its isomer from the ester of pseudomonic acid by preparative layer silica gel chromatography; and
   b. isolating the pseudomonic acid ester from the resulting mixture by crystallisation.

12. A process for the production of pseudomonic acid in substantially pure form, which process comprises growing *Pseudomonas fluorescens* under aerobic conditions on or in a culture medium containing inorganic salts and sources of assimilable carbon and nitrogen until the culture medium exhibits at least detectable antibacterial activity, thereafter adding a source of barium ions to the culture and removing the resultant precipitated material therefrom, extracting the culture medium with an organic solvent for the active materials dissolved in the culture medium, extracting the resultant organic solution with an aqueous alkaline solution, esterifying the active fraction, thereby producing a mixture of esters of three different acids, separating the ester of pseudomonic acid from the mixture and de-esterifying said ester, thereby producing pseudomonic acid.

13. A process according to claim 12, wherein the active fraction is methylated, thereby producing a mixture of methyl ester.

14. A process according to claim 12 wherein the ester of pseudomonic acid is separated from the mixture of esters by preparative layer silica gel chromatography.

* * * * *